US011229360B2

(12) United States Patent
Boud

(10) Patent No.: US 11,229,360 B2
(45) Date of Patent: Jan. 25, 2022

(54) COMMUNICATION OF PARENT PHYSIOLOGICAL DATA TO INFANT

(71) Applicant: Life-Line Products, LLC, Altoona, WI (US)

(72) Inventor: Eric Boud, Altoona, WI (US)

(73) Assignee: Life-Line Products, LLC, Altoona, WI (US)

( * ) Notice: Subject to any disclaimer, the term of this patent is extended or adjusted under 35 U.S.C. 154(b) by 0 days.

(21) Appl. No.: 17/120,925

(22) Filed: Dec. 14, 2020

(65) Prior Publication Data

US 2021/0259549 A1 Aug. 26, 2021

Related U.S. Application Data

(60) Provisional application No. 62/979,402, filed on Feb. 20, 2020.

(51) Int. Cl.
*A61B 5/00* (2006.01)
*A61B 5/0255* (2006.01)

(52) U.S. Cl.
CPC .......... *A61B 5/0011* (2013.01); *A61B 5/0015* (2013.01); *A61B 5/0022* (2013.01); *A61B 5/0255* (2013.01); *A61B 5/6801* (2013.01); *A61B 5/7203* (2013.01); *A61B 5/7275* (2013.01); *A61B 5/7475* (2013.01)

(58) Field of Classification Search
CPC ... A61B 5/0011; A61B 5/0015; A61B 5/0022; A61B 5/7475; A61B 5/0255; A61B 5/7275; A61B 5/7203; A61B 5/6801
See application file for complete search history.

(56) References Cited

U.S. PATENT DOCUMENTS

| | | | | |
|---|---|---|---|---|
| 6,004,259 A | * | 12/1999 | Sedaros | A61M 21/00 600/28 |
| 7,475,441 B1 | * | 1/2009 | Soberal | A47D 9/02 5/655 |
| 9,155,468 B2 | | 10/2015 | Montgomery | |
| 9,604,029 B2 | | 3/2017 | Alamos et al. | |
| 9,662,257 B1 | | 5/2017 | Fassihi et al. | |

(Continued)

OTHER PUBLICATIONS

Bischof et al.: "Samsung: Voices of Life | Unit 9", 2020, https://www.unit9.com/project/samsung-voices-life/.

*Primary Examiner* — Eugene T Wu
(74) *Attorney, Agent, or Firm* — Miller IP Law

(57) ABSTRACT

Communication of parent physiological data to an infant may include a first interface device which includes a sensor to record physiological data associated with a heartbeat of a parent, a processor to receive the physiological data from the sensor, and a transceiver; a server which receives the physiological data from the transceiver, accesses an instance of the physiological data from a replay storage location during a loss of communication, assigns a unique identifier, processes the physiological data, modifies the physiological data to be within an allowable threshold or accesses physiological data within the allowable threshold when the physiological data is outside an allowable threshold, filters the physiological data to apply an effect, and transmits the physiological data based on the unique identifier; and a second interface device which includes a transceiver to receive the physiological data and a communication element to communicate the physiological data to the infant.

17 Claims, 5 Drawing Sheets

(56) References Cited

U.S. PATENT DOCUMENTS

| | | |
|---|---|---|
| 10,166,161 B2 | 1/2019 | Fassihi et al. |
| 2003/0067391 A1* | 4/2003 | Fitzgerald .......... G08B 21/0208 340/573.1 |
| 2004/0068158 A1 | 4/2004 | Bennett |
| 2013/0096368 A1* | 4/2013 | Devroey ................ A61B 7/003 600/28 |
| 2014/0275742 A1* | 9/2014 | Andrew ................ A41B 13/06 600/28 |
| 2014/0330070 A1* | 11/2014 | Anabalon Alamos ....................... A61M 21/02 600/27 |

* cited by examiner

COMMUNICATION OF PARENT PHYSIOLOGICAL DATA TO INFANT

CROSS-REFERENCE TO RELATED APPLICATIONS

The present application claims priority to U.S. Provisional Patent Application No. 62/979,402 entitled "METHOD FOR SECURE COMMUNICATION OF PHYSIOLOGICAL DATA", filed on 20 Feb. 2020. The entire contents of the above-listed application are hereby incorporated by reference for all purposes.

BACKGROUND

Communication is a very important part of how people bond and connect with each other, animals, or other loved ones. This communication comes in many different forms such as verbal, non-verbal, physical, and visual communication.

However, there are often situations or obstacles that render various forms of communication inappropriate or impossible. Some of the variables that impact available channels of communication may include facility type, disability of participants, developmental level of participants, or geographic separation. Such variables can prevent a person from communicating with another, thus preventing the bonding and connection that may be desired and beneficial for physical and mental health.

BRIEF DESCRIPTION OF THE DRAWINGS

The present description will be understood more fully when viewed in conjunction with the accompanying drawings of various examples of communication of parent physiological data to an infant. The description is not meant to limit the physiological data communication to the specific examples. Rather, the specific examples depicted and described are provided for explanation and understanding of physiological data communication. Throughout the description, each of the drawings may be referred to as a drawing, figure, and/or FIG.

DETAILED DESCRIPTION

Figure 1:
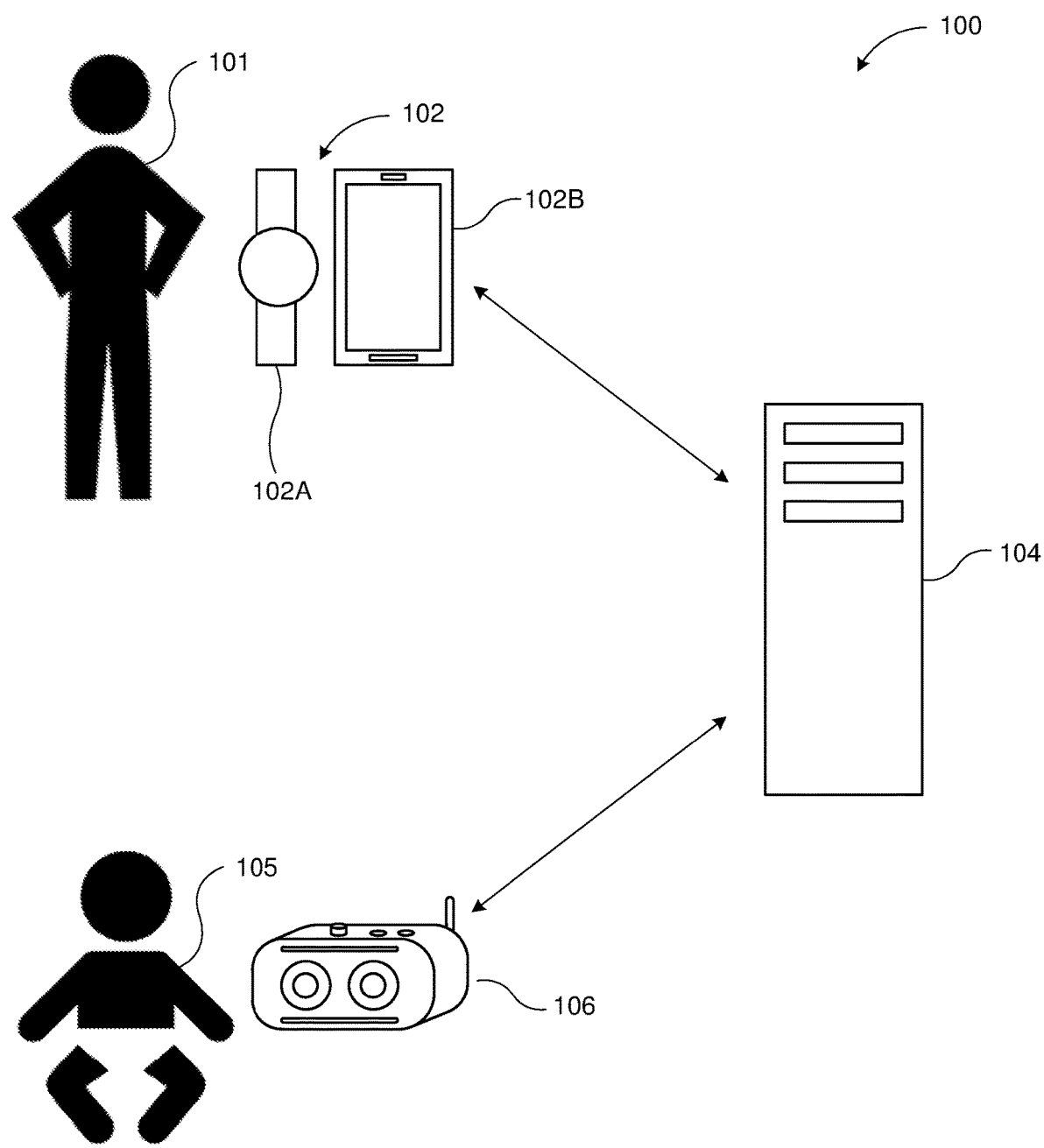
FIG. 1 illustrates a system for physiological data communication, according to an embodiment.

Communication of parent physiological data to an infant, as disclosed herein, will become better understood through a review of the following detailed description in conjunction with the figures. The detailed description and figures provide merely examples of the various embodiments of the communication of parent physiological data to an infant. Many variations are contemplated for different applications and design considerations; however, for the sake of brevity and clarity, all the contemplated variations may not be individually described in the following detailed description. Those skilled in the art will understand how the disclosed examples may be varied, modified, and altered and not depart in substance from the scope of the examples described herein.

Conventional infant care arrangements for physiologically compromised infants restrict parental contact and interaction with infants. Generally, the restriction of interaction is intended to reduce the chance of infection which may impede or otherwise disrupt the health and development of the infant. This is particularly relevant in intensive care scenarios. An infant in a neonatal intensive care unit (NICU) is isolated from contact with the parents as infants qualifying for this level of care are especially vulnerable. This leaves the parent(s) feeling helpless as they are unable to interact with their child and provide care and helpful stimulus to them during such a stressful and difficult time. It also leaves the infant alone and isolated from its parents. Additionally, there are strict requirements for communication in an intensive care environment, as well as other care environments, which make the use of technology difficult.

Implementations of the communication of parent physiological data to an infant, as described and claimed herein, may address some or all of the problems described above. Embodiments for communication of parent physiological data to an infant described herein may include the ability to provide pre-recorded or real-time physiological data from a parent and transmit the physiological data to the infant. The physiological data may include a heartbeat, voice, gut sound, breathing, walking or other movement sound, and so forth. The recorded physiological data may be modified or have safeguards put in place prior to sending to a user at a location remote from the parent. For example, the physiological data may be modified to simulate a womb environment, adjust volume, provide continuity, reduce background noise, or reduce unwanted frequencies or other sound components. In another example, the physiological data may be modified to adjust a particular component or number of components of the physiological data. A heartrate may be increased or decreased to fit an allowable range, a breathing pattern may be adjusted, or so forth.

The physiological data may be provided to the infant to improve the wellbeing of the infant by assuring the infant of the wellbeing of the parent as interpreted by the physiological data, provide a calming effect, instill a feeling of security, provide a familiar environment or stimulus, or so forth. For example, infants under the care of hospital facilities may benefit from the transmission of a parent's heartbeat, voice, gut sounds, breathing, or so forth. Some studies suggest that development and wellbeing of the child may be improved when provided with stimuli based on the physiological data of the parent.

Embodiments described herein may allow for real-time or substantially real-time provision of the physiological data of the parent to the infant. If the physiological data exceeds a predetermined threshold or is outside an allowable range, the physiological data may be modified to avoid causing undue stress or excitement in the infant. For example, if the heartbeat of the parent exceeds a beats-per-minute threshold, the heartbeat may be modified to reduce the heartrate, or a pre-recorded heartbeat may be transmitted in lieu of the non-compliant heartbeat. Similarly, if a heartbeat, breathing pattern, etc. is too high or too low (outside an allowable range), it may be modified to fit within the allowable range or recorded data from a replay storage location may be used in place of the physiological data detected. Additionally, if signal is lost or communication between the parent and the infant otherwise breaks down, prerecorded physiological data may be played to avoid a perception by the infant that the parent is under stress or otherwise compromised.

Embodiments described herein also conform to the stringent communication requirements in place in care facilities and allow a parent to be away from the care facility and remain in contact with their child, providing both beneficial stimulus for the child as well as peace of mind or comfort for the parent in knowing that they are providing a benefit for their child during a relatively high-stress experience. This may improve mental health and assist in working through adverse conditions such as post-partum depression.

FIG. 1 illustrates a system 100 for communication of parent 101 physiological data to an infant 105, according to an embodiment. Embodiment described herein allow for recording of physiological data from a parent 101 and communication of the parent's physiological data to an infant 105 in compliance with strict communication requirements to provide comfort and developmental benefits to the second user 105.

In the illustrated embodiment, the system 100 includes a first interface device 102, a server 104, and a second interface device 106. The first interface device 102 may be configured to sense a physiological characteristic of the parent 101. For example, the first interface device 102 may include a sensor to detect a heartbeat, voice, gut sounds, breathing, walking or other movement sounds, and so forth. The first interface device 102 may also be configured to transmit the physiological data to the server 104.

In some embodiments, the first interface device 102 is a wearable device 102A. In other embodiments, the first interface device 102 is a portable device 102B. For example, the portable device 102B may be a phone, tablet, laptop, or so forth. In some embodiments, the first interface device 102 may be a computer, recorder, or other portable or non-portable device. In some embodiments, the first interface device 102 communicates directly with the server 104. In other embodiments, the first interface device 102 communicates, at least in part, with an intermediate device such as a phone, computer, tablet, or so forth. In some embodiments, the intermediate device provides communication to the server 104. In other embodiments, the intermediate device and the first interface device 102 both communicate with the server 104.

The first interface device 102 allows a parent 101 to record physiological data. In some embodiments, the physiological data is sent, by the first interface device 102, to the server 104. The server 104 may receive the physiological data from the first interface device 102 and perform additional operations on the physiological data. For example, the server 104 may assign a unique identifier to the physiological data. The unique identifier may associate the physiological data with the first interface device 102 or with the parent 101. The server 104 may be local to the first interface device 102 or the second interface device 106 or remote to one or both of the first interface device 102 and the second interface device 106. In some embodiments, the server 104 may be a hardware-based server. In some embodiments, the server 104 may be a software-based server. For example, the server 104 may be a cloud-based server or other online or distributed resource server. In other embodiments, the server 104 may be a network attached server coupled directly to one of the first interface device 102 or the second interface device 106 via a singular network or indirectly via multiple communication networks.

In some embodiments, the server 104 processes the physiological data to comply with a communication standard. The communication standard may be a wireless communication format or may be a security requirement imposed by a broadcast location of the second interface device 106. For example, a hospital may have strict communication requirements that may involve security of the transmission, signal or device interference risks of the transmission, and so forth. Some embodiments of the server 104 may filter the physiological data to apply an effect to the physiological data. For example, the physiological data may be filtered to reduce a background noise, unintentional components, specific frequencies, or so forth. The server 104 may also filter the physiological data to apply a volume control to the physiological data. This may be particularly beneficial for use in a neonatal intensive care unit (NICU) of a hospital or other sensitive broadcast location.

The server 104 may be configured to store an instance of the live data set or first data set of the physiological data to a replay storage location on the server 104 or a device or location separate from the server 104 to form a second data set. In some embodiments, the server 104 may be configured to store the second data set of the physiological data for use in response to an interruption of the live data set from the first interface device or in response to detection that the physiological data from the first interface device 102 exceeds a threshold or is otherwise outside of an allowable range. For example, the server 104 may store physiological data corresponding to a resting heartrate for use when the detected heartrate is too high or too low. In some embodiments, the physiological data may be modified to form a third data set or modified data set. The physiological data may also be replaced with data from the second data set that is within the allowable range until it is determined that the live data set of the physiological data has returned to a level within the allowable range. For example, the parent may go for a run and forget that they are transmitting their heartbeat to the infant. As the system 100 detects the elevated heartrate as exceeding the allowable range, the physiological data may be replaced with a second data set corresponding to a resting heart rate or the heartbeat may be artificially slowed to form a third or modified data set that is within the allowable range until the parent has finished their run and their heartrate live data set has returned to a level within the allowable range at which time, transmission of the live data set would resume. Another example may include if the parent is asleep and their heartrate drops to a level which is below the allowable range. The system 100 may similarly replace or modify the heartbeat to bring it within the allowable range until the heartrate of the parent returns to the allowable range. In some embodiments, the allowable range may be determined by a parent. In other embodiments, the allowable range may be determined by another care provider such as a nurse, doctor, administrator, technician, or so forth.

In some embodiments, the physiological data may be filtered to apply an effect to the physiological data to mimic or simulate a womb environment. For example, the filter applied may intake a heartbeat and modify the heartbeat to simulate how it would sound to an unborn child in the womb. This filter may also be applied to breathing, music, voice, gut sounds, walking or other movement sounds, and so forth.

The server 104 may also be configured to transmit the physiological data to the broadcast location. The transmission may target the second interface device 106 based on the unique identifier applied to the physiological data. In some embodiments, the second interface device 106 may be placed at the broadcast location. The second interface device 106 may receive the physiological data from the server 104 and communicate the physiological data to an infant 105.

The physiological data may be communicated in compliance with the communication standard corresponding to the broadcast location and may have an applied effect.

The second interface device 106 may be positioned proximate the infant 105 to provide stimulus to the infant 105 based on the physiological data of the parent 101. The stimulus provided to the infant 105 may be at least one of auditory, visual, or tactile. For example, the second interface device 106 may be positioned proximate the infant 105 and configured to communicate the physiological data of the parent 101 to the infant 105 to simulate a womb environment for the infant 105. In the case of an infant 105, this effect may provide a calming or developmental benefit to the infant. In one example, the infant 105 may be a patient in the neonatal intensive care unit (NICU) of a hospital. A parent may be the parent 101 and may provide the physiological data to the second interface device 106 via the first interface device 102 and through the server 104. The physiological data may be a heartbeat, voice, breathing sound, gut sound, or so forth. In some embodiments, the second interface device 106 is configured for placement proximate a location of the infant. For example, the second interface device 106 may be configured for placement outside a bed or other structure housing the infant, inside the bed or other structure with the infant, or otherwise positioned to communicate the physiological data to the infant.

In some embodiments, the second interface device 106 is configured to output stimulus. In other embodiments, the second interface device 106 is configured to output stimulus and detect or record incoming data at the second interface device 106. For example, the second interface device 106 may record sound or other input and transmit that input to the first interface device 102 via the server 104 or directly. In this manner, a user may receive an image, sound, physiological data, vital information, caregiver information, or so forth via the system 100. In some embodiments, the input provided to the user may be automatically or manually filtered, updated, selected for transmission, or so forth. In some embodiments, the second interface device 106 may include a receiver and a transmitter in a unified device. In other embodiments, the receiver of the second interface device 106 may be separate from the transmitter of the second interface device 106. For example, the receiver of the second interface device 106 may be placed at a first location to receive data and relay the data to a transmitter of the second interface device 106 which is placed at a second location distinct from the first location. In some examples, the receiver may be plugged into a power outlet to have constant power while the transmitter may be a wireless speaker placed near the infant. The speaker or transmitter may be wireless, rechargeable, have a corresponding constant power source, or so forth.

Figure 2:
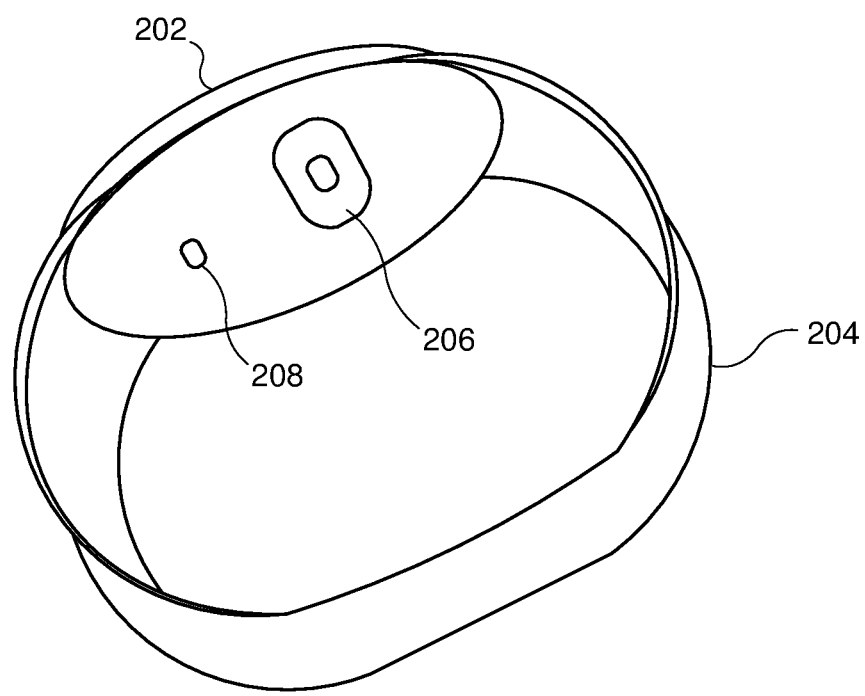
FIG. 2 illustrates a wearable device embodiment of the first interface device of the system of FIG. 1, according to an embodiment.

FIG. 2 illustrates a wearable device 102A embodiment of the first interface device 102 of the system 100 of FIG. 1, according to an embodiment. The first interface device 102 allows for recording of physiological data from a parent 101 so that the physiological data may be provided to an infant 105. For example, physiological data from a mother may be provided to her child. This may provide a calming effect or aid in the physical and mental development of the child. Additionally, a portability or ease of use of the first interface device 102 may allow for frequent real-time recording and transmission of physiological data from the parent 101 to the infant 105. For example, a mother may wear the first interface device 102 to provide a constant feed of physiological data to her child.

In some embodiments, the wearable device 102A includes a body 202 and a strap 204. The strap 204 may be configured to attach the body 202 to a user's wrist or other location. In some embodiments, the strap 204 couples to be body 202 to position the body 202 of the wearable device 102A to record physiological data. In some embodiments, the wearable device 102A includes a first sensor 206 and a second sensor 208. The first sensor 206 may include a heartrate sensor or other biometric or physiological sensor. The second sensor 208 may include a microphone or other audio sensor.

In some embodiments, the wearable device 102A includes two sensors. In other embodiments, the wearable device 102A includes a single sensor or more than two sensors. In some embodiments, one or more sensors may be incorporated in the device 102B for supplemental or stand-alone detection. In some embodiments, the first sensor 206 tracks a heartbeat, heartrate, or other physiological data which may be transmitted by the wearable device 102A. In other embodiments, the wearable device 102A records the heartbeat, heartrate, or other physiological data and displays a representation of the physiological data to a display screen on the body 202 of the wearable device 102A. In some embodiments, the wearable device 102A may facilitate manipulation or approval/rejection of the physiological data. In other embodiments, the wearable device 102A may allow a user to select a type of physiological data to send. For example, the wearable device 102A may provide that ability to select a recorded or detected heartbeat, heartrate, voice, gut sound, breathing, walking or other movement sound, or so forth In some embodiments, the wearable device 102A may allow the user to initiate a monitoring or detecting mode. For example, the user may interface with the wearable device 102A to start a feed of a heartbeat, make a heartbeat recording, make a voice recording or feed, and so forth. In some embodiments, the wearable device 102A records or otherwise provides physiological data for a predetermined amount of time. In other embodiments, the wearable device 102A collects physiological data until the user stops the collection.

Figure 3:
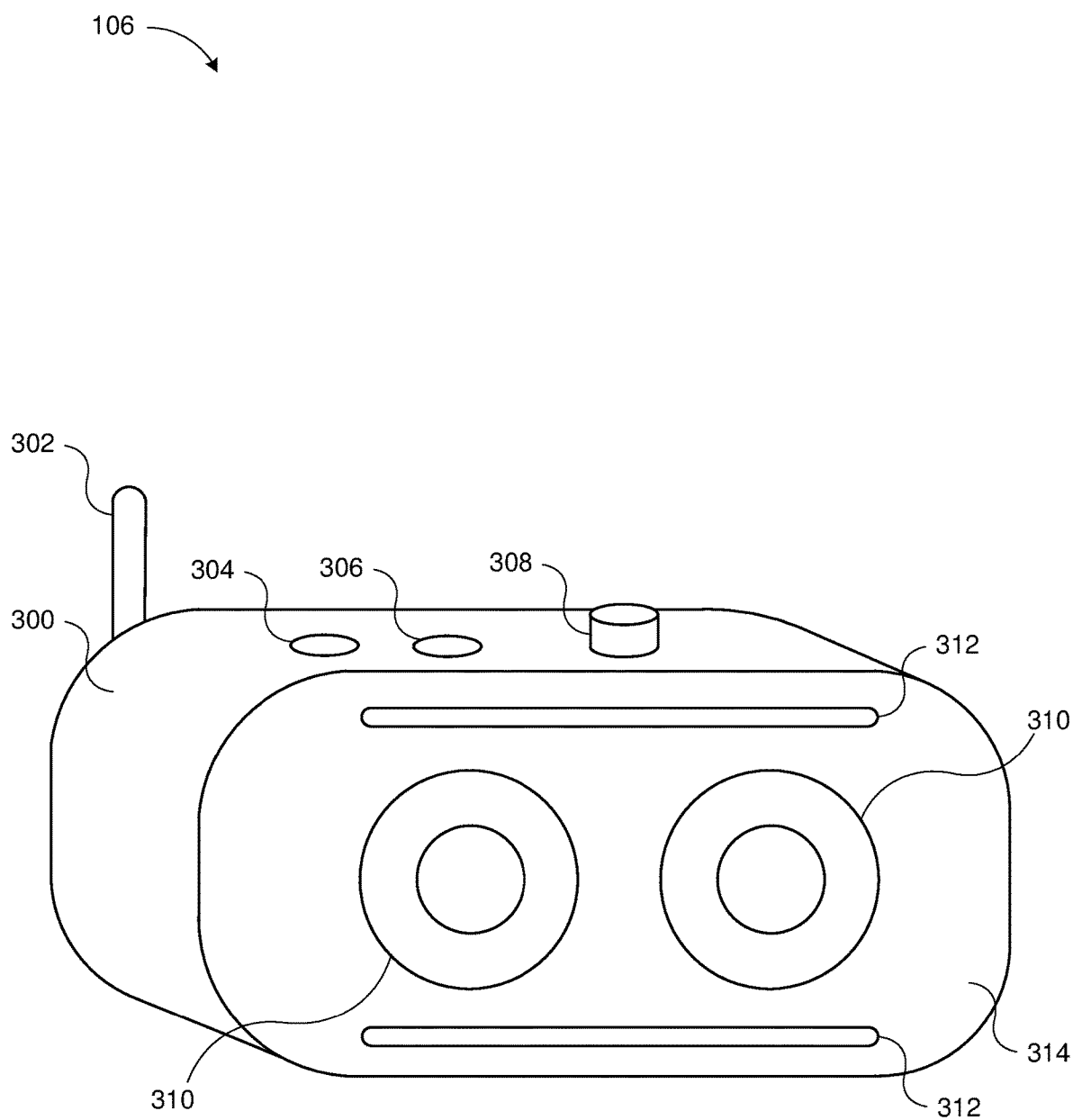
FIG. 3 illustrates the second interface device of the system of FIG. 1, according to an embodiment.

FIG. 3 illustrates the second interface device 106 of the system 100 of FIG. 1, according to an embodiment. Some embodiments, of the second interface device 106 allow for broadcasting of the physiological data in compliance with a sensitive and highly controlled environment. The second interface device 106 may provide beneficial stimulus to an infant 105 and give parents or other caregivers peace of mind knowing that they are providing a benefit to the infant 105.

In some embodiments, the second interface device 106 may include a body 300, an antenna 302, a power control 304, a communication control 306, and a volume control 308. The second interface device 106 may also include a speaker 310 and a lighting element 312 positioned on a face 314 of the second interface device 106. The body 300 of the second interface device 106 may include materials and construction which is safe for use. For example, the body 300 may include materials and/or construction to reduce a likelihood of snags, splintering, shock, burn, scratching, or other risks. Additionally, the body 300 may be easy to clean. In some embodiments, the body 300 and may include antimicrobial or antibacterial additives or coatings. For example, some embodiments may include a polyether ether ketone (PEEK) plastic with an antimicrobial additive. In some embodiments, the second interface device 106 includes electronic shielding. For example, the electronic shielding may protect against electrical discharge, unintended radio wave transmission or other radiation, electrical interference, unwanted signal access, and so forth.

In some embodiments, the antenna 302 is configured to receive transmitted data. The antenna 302 may be configured to facilitate communications in compliance with a communication standard corresponding to the broadcast location. For example, the antenna 302 may be configured to comply with a hospital communication protocol or reduce the chance of interference by communications sent from or received by the antenna 302.

Embodiments of the antenna 302 may come in any form, shape, or function and may include the ability to receive the transmission of data via a wireless network. For example, the antenna 302 may be configured to communicate via a cellular network, local wireless network, or other proprietary or non-proprietary network or communication protocol. The antenna 302 and the physiological data may be configured to comply with privacy regulations such as HIPAA or the like or to comply with wireless communication standards and avoid interference with existing systems.

In some embodiments, the power control 304 operates an on/off function of the second interface device 106. In some embodiments, the powered on or off state of the second interface device 106 is controlled locally to the second interface device 106. In other embodiments, the powered on or off state of the second interface device 106 may be controlled remotely and communicated to the second interface device 106 via the antenna 302 or otherwise.

In some embodiments, the communication control 306 may allow for initiation of a link between the second interface device 106 and another device. For example, the communication control 306 may allow for pairing of the second interface device 106 with a sensor, transmitter, monitor, remote control, or so forth.

In some embodiments, the volume control 308 allows for local volume adjustments to be made at the second interface device 106. The volume control 306 may override a volume adjustment made by the server 104 or at the first interface device 102. In some embodiments, the volume control 308 may allow a user at the second interface device 106 to control a volume level to be appropriate for the environment and situation in which the second interface device 106 may be found. In other embodiments, the volume control is applied by the server 104 based on the location and/or environment of the second interface device 106. For example, a predetermined decibel or other threshold limit may be applied and the server 104 may modify the physiological data to conform to the threshold limit in response to detection that the physiological data exceeds the threshold. In other embodiments, the volume level applied by the server 104 may be overridden by the volume control 308. In other embodiments, the server 104, first interface device 102, or second interface device 106 may apply an acoustic analysis to identify other components of the physiological data and, in response to the identification of the component, reduce, remove, replace, or enhance the component of the physiological data based on a threshold, target, or other setting. For example, an infant in a NICU environment may tolerate or the environment may allow for a first volume level while an infant in another unit within the hospital or other facility may tolerate, or the unit may allow, a second volume level. Other volume levels may be selected or determined based on the health and sensitivity of the infant and/or the requirements of the location or environment in which the infant is located.

It should be understood that many potential methods exist to control the basic functions of the second interface device 106. For example, one or more buttons, knobs, and/or controls may be in touch sensitive, tactile, mobile or web application reactive, capacitive, voice control, or so forth. In some embodiments, the second interface device 106 may include a speaker 310 disposed in a face 314 of the second interface device 106. In other embodiments, the second interface device 106 may include a lighting element 312 disposed in the face 314 of the second interface device 106. The speaker 310 may provide audible or inaudible vibrational stimulus to a user. For example, the speaker 310 may be configured to communicate an audible heartbeat or other sound to a user. The speaker 310 may also communicate the heartbeat or other stimulus to the user via an inaudible vibration which may be communicated directly or indirectly to the user.

In some embodiments, the lighting elements 312 may illuminate to present a particular lighting pattern. For example, the lighting elements 312 may illuminate in a particular color or combination of colors. The colors may be coordinated with a characteristic of the physiological data or an input at the first interface device 102 or the second interface device 106. The lighting elements 312 may also be configured to provide visual displays of words, pictures, video, movement, or so forth.

While particular components are shown in conjunction with the second interface device 106, other components may be included. For example, the second interface device 106 may include a microphone, camera, sensor, vibratory or other motors, visual displays for words, pictures, or so forth, heaters, coolers, olfactory features, or so forth. Some embodiments of the receiver may be wireless. Other embodiments may be wired for at least one of power, data, synchronization, control, or so forth. In some embodiments, the second interface device 106 may be powered through the use of battery, solar power, capacitor, induction, wireless power transmission, charging cord, or any other power supply arrangement. In some embodiments, the second interface device 106 includes hardware for hanging, mounting, orienting, securing, or otherwise situating the second interface device 106 relative to a surface or structure. For example, the second interface device 106 may include hardware to facilitate mounting the second interface device 106 on, in, or near a structure housing the infant.

In some embodiments, the second user interface device 106 may be a communication element that is in communication with a separate local transceiver. The transceiver may be placed separate from the communication element to receive the data and transmit the data wirelessly to the communication element to the infant. For example, the transceiver may be plugged into a power source (e.g., a wall outlet) to receive constant power while the communication element may be a wireless device with an internal power source allowing the communication element to be readily placed near the infant with intermittent recharging or power source replacement or also having access to a constant power source. In other embodiments, the second interface device 106 may include the transceiver and communication element in a single unified arrangement.

Figure 4:
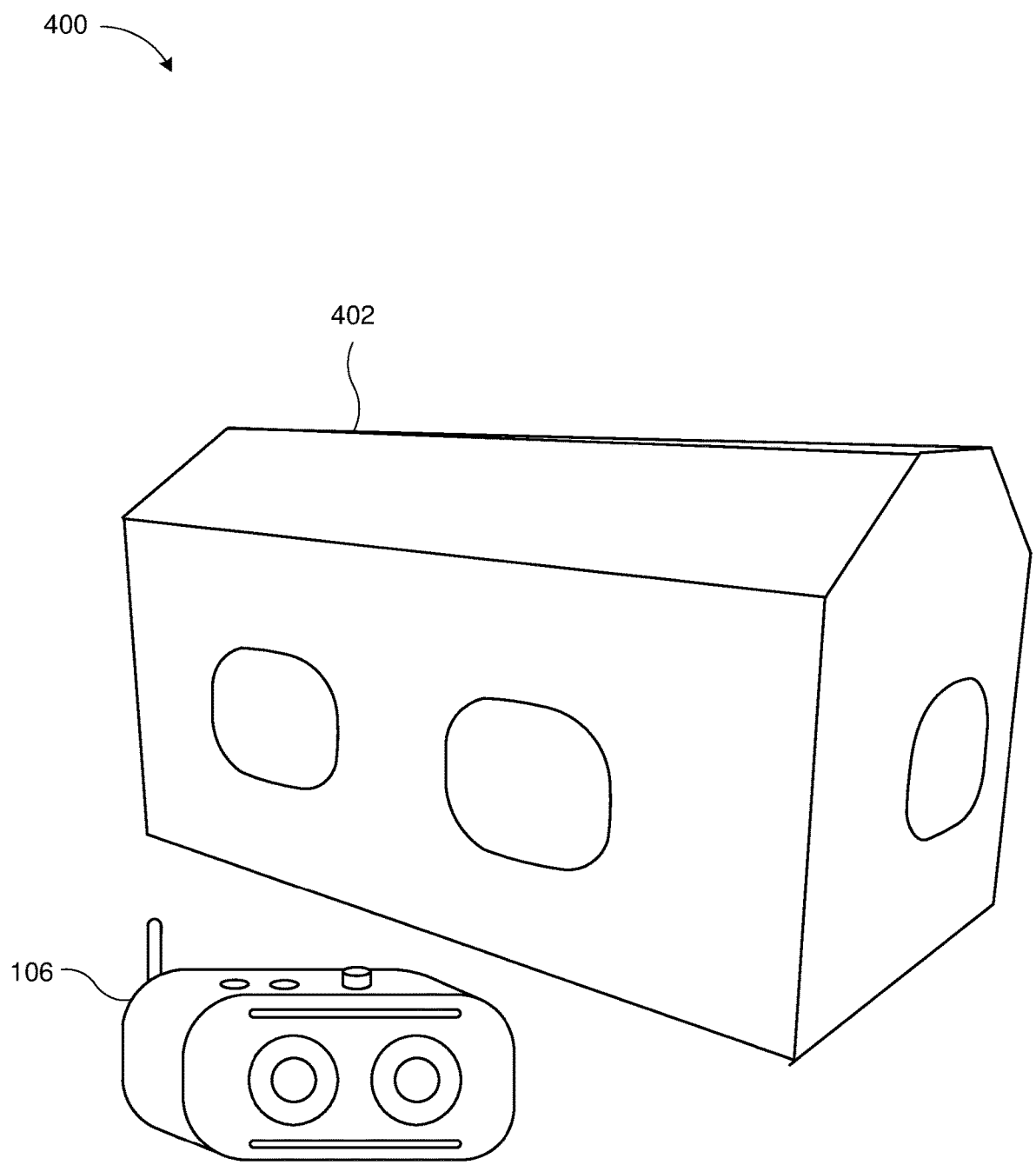
FIG. 4 illustrates the second interface device of the system of FIG. 1 in a broadcast location, according to an embodiment.

FIG. 4 illustrates the second interface device 106 of the system 100 of FIG. 1 in a broadcast location 400, according to an embodiment. In some embodiments, the second interface device 106 provides a unique ability to share physiological data with a child while the child is kept away from parents. The ability to provide that physiological data in the form of a heartbeat, voice, and so forth may provide beneficial comfort and/or aids in the development of the child. The second interface device 106 is capable of providing a familiar element in a place that is purposefully devoid of human contact and stimulus during such a stressful and difficult time.

The illustrated embodiment includes the second interface device 106 positioned at the broadcast location 400 to be proximate an incubator 402. The incubator 402 may be a neonatal intensive care unit (NICU) incubator. In some embodiments, the second interface device 106 provides stimulus to user in the incubator 402. The stimulus may take the form of sound, light, vibration, and so forth. In some embodiments, the second interface device 106 may be positioned at a distance from the incubator 402 to direct the stimulus towards the incubator 402. In other embodiments, the second interface device 106 may be configured to contact the incubator 402 and direct the stimulus into the incubator 402. In some embodiments, the second interface device 106 utilizes a characteristic or structure of the incubator 402 to communicate the stimulus to an interior of the incubator 402. For example, the second interface device 106 may be configured to utilize a resonance of the incubator 402.

In some embodiments, the second interface device 106 is separate from the incubator 402. In other embodiments, the second interface device 106 is integrated with the incubator 402. For example, the second interface device 106 may be incorporated into a wall or ceiling of the incubator 402. The second interface device 106 may also be incorporated into a floor or other component of the incubator 402 or an associated structure such as a cart supporting the incubator 402.

Figure 5:
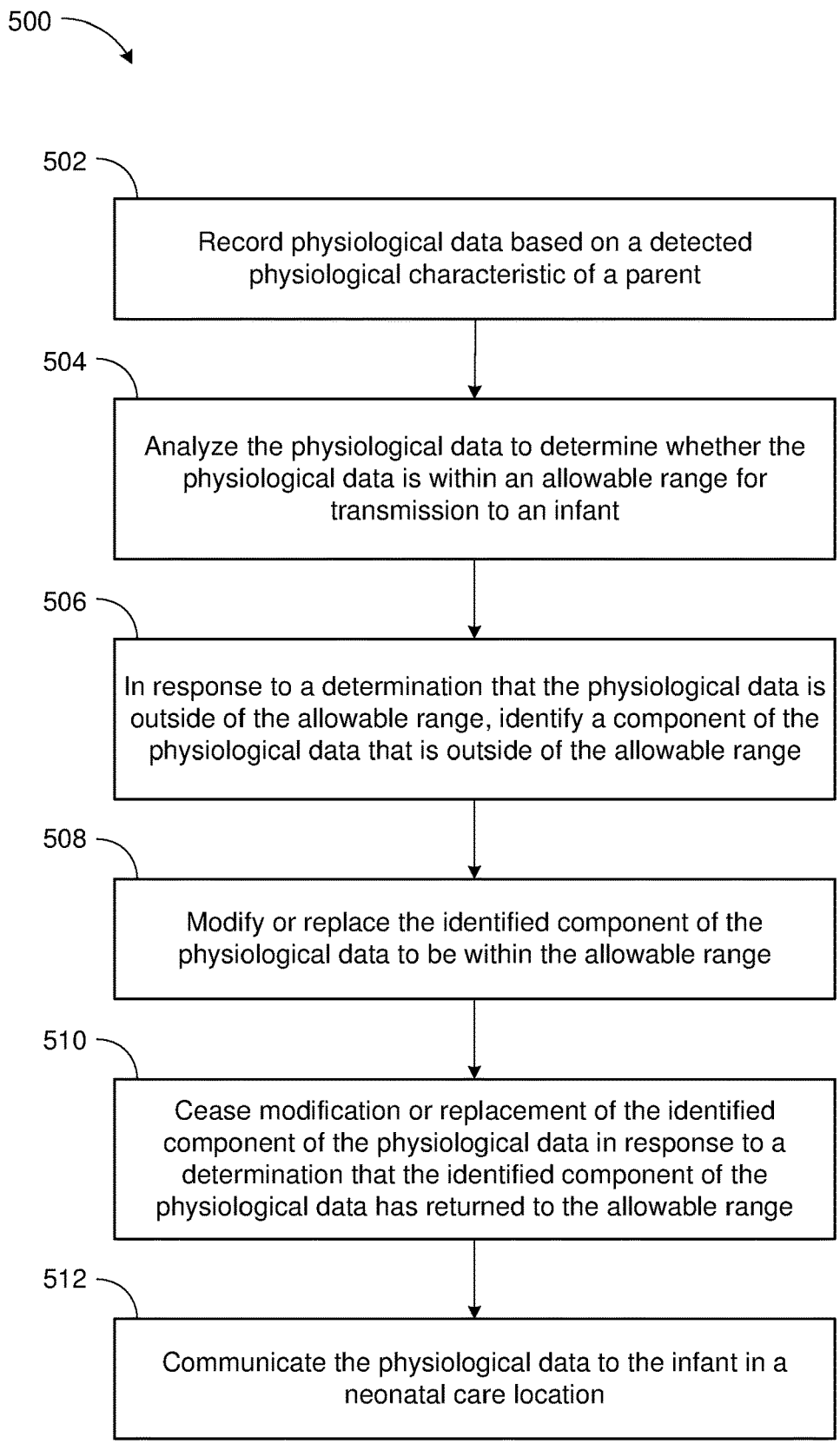
FIG. 5 illustrates a method for providing physiological data to an infant, according to an embodiment.

FIG. 5 illustrates a method 500 for providing physiological data to an infant, according to an embodiment. Some embodiments of the method 500 described herein provide for contact between a parent and child though the child may be isolated from the parent in a neonatal care location. Providing the stimulus aids the child in development and reduces potential stress events. Additionally, allowing the parent to provide care and love to their child while removed from the child may improve a mental and emotional state of the parent.

The method 500 may include recording physiological data based on a detected physiological characteristic of a parent (Block 502). For example, the parent 101 may be a parent 101 wearing or otherwise using a first interface device 102 to record a heartbeat, voice, gut sounds, breathing, walking or other movement sounds, and so forth. The method 500 may include analyzing the physiological data to determine whether the physiological data is within an allowable range for transmission to an infant (Block 504). For example, the physiological data may be run through an acoustic or other analysis to compare one or more components of the physiological data to a corresponding allowable range for safely transmitting the physiological data to the infant.

The method 500 may include identifying a component of the physiological data that is outside of the allowable range in response to a determination that the physiological data is outside of the allowable range (Block 506). For example, the server 104 may detect a heartrate within the physiological data and determine that the heartrate is low as to be below the allowable range.

The method 500 may include modifying or replacing the identified component of the physiological data to be within the allowable range (Block 508). For example, if the identified component is too loud, it may be reduced; too soft, amplified. If too fast, the identified component may be slowed; too slow, sped up, and so forth.

The method 500 may include ceasing modification or replacement of the identified component of the physiological data in response to a determination that the identified component of the physiological data has returned to the allowable range (Block 510). For example, if the identified component is a rate of a heartbeat and the rate returns to the allowable range, the heartbeat may be transmitted again without the need for modification.

The method 500 may include communicating the physiological data to the infant 105 in a neonatal care location (Block 512). For example, the modified physiological data may be transmitted to the second interface device 106 which may be configured to deliver at least one of an audible, visual, haptic, or other stimulus to the infant in the neonatal care location.

In some examples, the identified component may correspond to only a portion of the physiological data communicated to the infant. Modification of the identified component of the physiological data may reduce a health risk to the infant that may occur from exposure of the infant to the physiological data. For example, the stress that may be induced by subjecting the infant to a heartbeat that is excessively high or a drop in a breathing pattern, or so forth.

A feature illustrated in one of the figures may be the same as or similar to a feature illustrated in another of the figures. Similarly, a feature described in connection with one of the figures may be the same as or similar to a feature described in connection with another of the figures. The same or similar reference characters may note the same or similar features unless expressly described otherwise. Additionally, the description of a particular figure may refer to a feature not shown in the particular figure. The feature may be illustrated in, and/or further described in connection with, another figure.

Elements of processes (i.e. methods) described herein may be executed in one or more ways such as by a human, by a processing device, by mechanisms operating automatically or under human control, and so forth. Additionally, although various elements of a process may be depicted in the figures in a particular order, the elements of the process may be performed in one or more different orders without departing from the substance and spirit of the disclosure herein.

The foregoing description sets forth numerous specific details such as examples of specific systems, components, methods and so forth, in order to provide a good understanding of several implementations. It will be apparent to one skilled in the art, however, that at least some implementations may be practiced without these specific details. In other instances, well-known components or methods are not described in detail or are presented in simple block diagram format in order to avoid unnecessarily obscuring the present implementations. Thus, the specific details set forth above are merely exemplary. Particular implementations may vary from these exemplary details and still be contemplated to be within the scope of the present implementations.

Related elements in the examples and/or embodiments described herein may be identical, similar, or dissimilar in different examples. For the sake of brevity and clarity, related elements may not be redundantly explained. Instead, the use of a same, similar, and/or related element names and/or reference characters may cue the reader that an element with a given name and/or associated reference character may be similar to another related element with the same, similar, and/or related element name and/or reference character in an example explained elsewhere herein. Elements specific to a given example may be described regarding that particular example. A person having ordinary skill in the art will understand that a given element need not be the same and/or similar to the specific portrayal of a related element in any given figure or example in order to share features of the related element.

It is to be understood that the foregoing description is intended to be illustrative and not restrictive. Many other implementations will be apparent to those of skill in the art upon reading and understanding the above description. The scope of the present implementations should, therefore, be determined with reference to the appended claims, along with the full scope of equivalents to which such claims are entitled.

The foregoing disclosure encompasses multiple distinct examples with independent utility. While these examples have been disclosed in a particular form, the specific examples disclosed and illustrated above are not to be considered in a limiting sense as numerous variations are possible. The subject matter disclosed herein includes novel and non-obvious combinations and sub-combinations of the various elements, features, functions and/or properties disclosed above both explicitly and inherently. Where the disclosure or subsequently filed claims recite "a" element, "a first" element, or any such equivalent term, the disclosure or claims is to be understood to incorporate one or more such elements, neither requiring nor excluding two or more of such elements.

As used herein "same" means sharing all features and "similar" means sharing a substantial number of features or sharing materially important features even if a substantial number of features are not shared. As used herein "may" should be interpreted in a permissive sense and should not be interpreted in an indefinite sense. Additionally, use of "is" regarding examples, elements, and/or features should be interpreted to be definite only regarding a specific example and should not be interpreted as definite regarding every example. Furthermore, references to "the disclosure" and/or "this disclosure" refer to the entirety of the writings of this document and the entirety of the accompanying illustrations, which extends to all the writings of each subsection of this document, including the Title, Background, Brief description of the Drawings, Detailed Description, Claims, Abstract, and any other document and/or resource incorporated herein by reference.

As used herein regarding a list, "and" forms a group inclusive of all the listed elements. For example, an example described as including A, B, C, and D is an example that includes A, includes B, includes C, and also includes D. As used herein regarding a list, "or" forms a list of elements, any of which may be included. For example, an example described as including A, B, C, or D is an example that includes any of the elements A, B, C, and D. Unless otherwise stated, an example including a list of alternatively-inclusive elements does not preclude other examples that include various combinations of some or all of the alternatively-inclusive elements. An example described using a list of alternatively inclusive elements includes at least one element of the listed elements. However, an example described using a list of alternatively inclusive elements does not preclude another example that includes all of the listed elements. And, an example described using a list of alternatively inclusive elements does not preclude another example that includes a combination of some of the listed elements. As used herein regarding a list, "and/or" forms a list of elements inclusive alone or in any combination. For example, an example described as including A, B, C, and/or D is an example that may include: A alone; A and B; A, B and C; A, B, C, and D; and so forth. The bounds of an "and/or" list are defined by the complete set of combinations and permutations for the list.

Where multiples of a particular element are shown in a FIG., and where it is clear that the element is duplicated throughout the FIG., only one label may be provided for the element, despite multiple instances of the element being present in the FIG. Accordingly, other instances in the FIG. of the element having identical or similar structure and/or function may not have been redundantly labeled. A person having ordinary skill in the art will recognize based on the disclosure herein redundant and/or duplicated elements of the same FIG. Despite this, redundant labeling may be included where helpful in clarifying the structure of the depicted examples.

The Applicant(s) reserves the right to submit claims directed to combinations and sub-combinations of the disclosed examples that are believed to be novel and non-obvious. Examples embodied in other combinations and sub-combinations of features, functions, elements and/or properties may be claimed through amendment of those claims or presentation of new claims in the present application or in a related application. Such amended or new claims, whether they are directed to the same example or a different example and whether they are different, broader, narrower or equal in scope to the original claims, are to be considered within the subject matter of the examples described herein.

The invention claimed is:

1. A system comprising:
a first interface device comprising:
a sensor configured to record physiological data associated with a heartbeat of a parent;
a processor configured to receive the physiological data from the sensor, wherein the physiological data corresponds to a physiological characteristic of the parent; and
a transceiver configured to communicate the physiological data;
a server configured to:
receive the physiological data from the first interface device, wherein the received physiological data forms a first data set;
in response to a loss of communication of the physiological data from the first interface device, access a stored instance of the physiological data previously stored to a replay storage location, wherein the stored instance of the physiological data forms a second data set;
assign a unique identifier to the physiological data to associate the physiological data with the first interface device;
process the physiological data to comply with a communication standard corresponding to a broadcast location;
in response to detection that the first data set received from the first interface device is outside an allowable threshold, modify the first data set to form a third data set that is within the allowable threshold or access the second data set, from the replay storage location, that is within the allowable threshold;
filter the physiological data to apply an effect to the physiological data; and
transmit the physiological data to the broadcast location based on the unique identifier; and
a second interface device configured to be positioned at the broadcast location and comprising:

a transceiver configured to receive the physiological data; and a communication element configured to communicate the physiological data to an infant in compliance with the communication standard corresponding to the broadcast location and with the effect applied.

2. The system of claim 1, wherein the server is further configured to:

detect a loss of communication from the first interface device;

replay the second data set; and resume transmission of the first data set from the first interface device when communication with the first interface device is restored.

3. The system of claim 1, wherein the physiological data further comprises a voice of the parent.

4. The system of claim 1, wherein the effect applied to the physiological data comprises removal of a component of the physiological data.

5. The system of claim 4, wherein the removal of the component of the physiological data comprises removal of background noise.

6. The system of claim 1, wherein the effect applied to the physiological data comprises a womb effect to simulate a womb environment at the broadcast location.

7. The system of claim 1, wherein the communication standard corresponding to the broadcast location comprises a volume level configured to accommodate a sensitivity of the infant or a requirement of the broadcast location.

8. A system comprising:

a first interface device comprising:

a sensor configured to record physiological data associated with a heartbeat of a parent;

a processor configured to receive the physiological data from the sensor, wherein the physiological data corresponds to a physiological characteristic of the parent; and a transceiver configured to communicate the physiological data; and a server configured to:

receive the physiological data from the first interface device, wherein the received physiological data forms a first data set;

in response to a loss of communication of the physiological data from the first interface device, access a stored instance of the physiological data previously stored to a replay storage location, wherein the stored instance of the physiological data forms a second data set;

assign a unique identifier to the physiological data to associate the physiological data with the first interface device;

process the physiological data to comply with a communication standard corresponding to an infant care location;

in response to detection that the first data set received from the first interface device is outside an allowable threshold, modify the first data set to form a third data set that is within the allowable threshold or access the second data set, from the replay storage location, that is within the allowable threshold;

filter the physiological data to apply an effect to the physiological data; and transmit the physiological data to the infant care location based on the unique identifier.

9. The system of claim 8, wherein the physiological data further comprises at least one of: a voice of the parent; data is indicative of respiration of the parent; or gut sounds of the parent.

10. The system of claim 8, wherein the physiological data further comprises: a voice of the parent; data is indicative of respiration of the parent; and gut sounds of the parent.

11. The system of claim 8, wherein the server is configured to encrypt the physiological data prior to transmission of the physiological data to the infant care location in compliance with a communications standard corresponding to the infant care location to reduce a possibility of violating a privacy regulation enforced at the infant care location.

12. The system of claim 8, wherein the first unique identifier further identifies a second interface device and distinguishes the second interface device from another interface device at the infant care location to avoid accidental interference with the other interface device.

13. A system comprising:

a first interface device comprising:

a sensor configured to record physiological data associated with a heartbeat of a parent;

a processor configured to receive the physiological data from the sensor, wherein the physiological data corresponds to a physiological characteristic of the parent; and a transceiver configured to communicate the physiological data; and a server configured to:

receive the physiological data from the first interface device, wherein the received physiological data forms a first data set;

in response to a loss of communication of the physiological data from the first interface device, access a stored instance of the physiological data previously stored to a replay storage location, wherein the stored instance of the physiological data forms a second data set; and transmit the physiological data to a broadcast location.

14. The system of claim 13, wherein the physiological data further comprises at least one of: a voice of the parent; data is indicative of respiration of the parent; or gut sounds of the parent.

15. The system of claim 13, wherein the physiological data further comprises: a voice of the parent; data is indicative of respiration of the parent; and gut sounds of the parent.

16. The system of claim 13, assign a unique identifier to the physiological data to associate the physiological data with the first interface device;

process the physiological data to comply with a communication standard corresponding to the broadcast location;

in response to detection that the first data set received from the first interface device is outside an allowable threshold, modify the first data set to form a third data set that is within the allowable threshold or access the second data set, from the replay storage location, that is within the allowable threshold; and filter the physiological data to apply an effect to the physiological data.

17. The system of claim 16, wherein modifying the first data set comprises:

applying a volume limit required by broadcast location;

slowing down a first heartbeat that is determined to be above a first threshold; or speeding up a second heartbeat that is determined to be below a second threshold.

\* \* \* \* \*